(12) United States Patent
Lane

(10) Patent No.: US 6,368,269 B1
(45) Date of Patent: Apr. 9, 2002

(54) APPARATUS FOR CONCURRENT ACTUATION OF MULTIPLE FOOT PEDAL OPERATED SWITCHES

(75) Inventor: Timothy G. Lane, Merritt Island, FL (US)

(73) Assignee: Tilane Corporation, Rockledge, FL (US)

( * ) Notice: Subject to any disclaimer, the term of this patent is extended or adjusted under 35 U.S.C. 154(b) by 0 days.

(21) Appl. No.: 08/734,487

(22) Filed: Oct. 21, 1996

Related U.S. Application Data

(63) Continuation of application No. 08/584,728, filed on Jan. 11, 1996, now abandoned, which is a continuation of application No. 08/199,334, filed on Feb. 22, 1994, now abandoned, which is a continuation-in-part of application No. 08/065,160, filed on May 20, 1993, now abandoned.

(51) Int. Cl.$^7$ .............................. A61B 1/04; G01N 23/04
(52) U.S. Cl. ...................... 600/126; 600/118; 200/86.5; 200/201; 378/63; 378/98; 378/115
(58) Field of Search ........................ 600/126; 200/86.5, 200/204.3, 201; 378/63, 98, 114, 115, 116, 117

(56) References Cited

U.S. PATENT DOCUMENTS

| | | | |
|---|---|---|---|
| 2,944,120 A | * 7/1960 | Ruben ........................ 200/86.5 |
| 3,017,497 A | * 1/1962 | Albright ................. 200/86.5 X |
| 3,327,662 A | * 6/1967 | Abate et al. ................ 200/86.5 |
| 3,448,606 A | 6/1969 | Flaherty et al. |
| 3,622,785 A | 11/1971 | Irwin et al. |
| 3,675,020 A | 7/1972 | Siedband et al. |
| 3,919,467 A | 11/1975 | Peugeot |
| 4,037,107 A | 7/1977 | Lutz et al. |
| 4,037,491 A | * 7/1977 | Newbold ............... 200/86.5 X |
| 4,058,833 A | 11/1977 | Meyer |
| 4,131,797 A | 12/1978 | Franke |
| 4,172,217 A | * 10/1979 | Miller ........................ 200/86.5 |
| 4,349,750 A | 9/1982 | Geurts |
| 4,358,855 A | 11/1982 | Szasz et al. |
| 4,383,328 A | 5/1983 | Kurihara et al. |
| 4,413,352 A | 11/1983 | Nishio |
| 4,504,858 A | 3/1985 | Franke |
| 4,544,949 A | 10/1985 | Kurihara |

(List continued on next page.)

FOREIGN PATENT DOCUMENTS

| | | |
|---|---|---|
| EP | 56235 | 5/1982 |
| JP | 63-88797 | 4/1988 |

*Primary Examiner*—John Mulcahy

(57) ABSTRACT

An apparatus is disclosed for coordinating the operation of multiple devices actuated by foot pedal operated switches. A housing has a lid movably mounted thereto and defines a recess therewithin. A foot pedal assembly has a pedal member which is downwardly movable and which is adapted to be depressed by downward pressure exerted by the foot of a user. The foot pedal assembly has a first switch operatively associated therewith which is actuated by a downward movement of the pedal member. The foot pedal assembly is disposed within the recess defined within the housing such that a downward movement of the lid displaces the pedal member of the foot pedal assembly to actuate the first switch. A second switch is disposed such that the downward movement of the lid of the housing also actuates the second switch. Downward movement of the lid actuates the first and second switches together to concurrently change the states of first and second devices operatively associated with the first and second switches. In one embodiment the second switch comprises a foot pedal operated switch, such that two foot pedal assemblies are positioned within the housing and actuated simultaneously upon a downward movement of the lid. In another embodiment the lid is divided into two sections, such that both of the switches are normally actuated concurrently, but one of the switches can be operated independently of the other if desired.

17 Claims, 6 Drawing Sheets

U.S. PATENT DOCUMENTS

| | | |
|---|---|---|
| 4,569,334 A | 2/1986 | Ohshiro |
| 4,658,413 A | 4/1987 | Nishioka et al. |
| 4,677,477 A | 6/1987 | Plut et al. |
| 4,821,117 A | 4/1989 | Sekiguchi |
| 4,993,404 A | 2/1991 | Lane |
| 5,029,016 A | 7/1991 | Hiyama et al. |
| 5,127,394 A | 7/1992 | Lane |

* cited by examiner

APPARATUS FOR CONCURRENT ACTUATION OF MULTIPLE FOOT PEDAL OPERATED SWITCHES

CROSS REFERENCE TO RELATED APPLICATION

This application is a continuation of application Ser. No. 08/584,728, filed Jan. 11, 1996, and now abandoned, which is a continuation of application Ser. No. 08/199,334 filed Feb. 22, 1994, and now abandoned, which is a continuation-in-part of application Ser. No. 08/065,160 filed May 20, 1993, and now abandoned.

TECHNICAL FIELD

The present invention relates generally to foot pedal operated switches and to an apparatus for concurrent actuation of multiple foot pedal operated switches. More specifically, the present invention relates to an apparatus for concurrent actuation of multiple foot pedals to coordinate the operation of devices actuated by foot pedal operated switches, for example, medical equipment such as a video endoscope or a video fluoroscope.

BACKGROUND OF THE INVENTION

Endoscopes have long been widely used in medical procedures for directly visualizing the interior of a canal or body cavity. A recent improvement on the endoscope is the video endoscope, wherein fiber optics permit the endoscopic view to be displayed on a video monitor. Video endoscopy provides a number of advantages over traditional endoscopy, including permitting more than one person at a time to observe the endoscopic view, permitting the physician to assume a more comfortable viewing angle, while permitting clearer still photographs or a videotape record to be made of the procedure.

Similarly, modern fluoroscopic technology presents advances over conventional radiography. In conventional radiography, X-rays are projected through a patient onto a photographic film which, when processed, will provide a fixed image of the patient'internal structure. In fluoroscopy, the X-ray sensitive photographic film is replaced by a fluorescent screen which, when subjected to X-radiation, produces a direct image of the object under investigation. Because the image on the fluorescent screen is usually so faint that it is difficult to visualize with the unaided eye, the screen image is usually photographed with a sensitive video camera. The video signal is then processed to increase the brightness of the image, and the image is displayed on a video fluoroscopy monitor for viewing by the physician. Fluoroscopy affords two primary advantages over conventional radiography: first, the image produced is direct, so there is no need for photographic processing; and second, the image is viewed in "real time", rather than as a still photograph or series of still photographs, and can thus show movement.

Surgical modalities are well known wherein video endoscopy is used in conjunction with dye-injection studies under fluoroscopy at various times during the procedure. Examples of such procedures include endoscopic management of biliary tract obstruction and endoscopic sphincterotomy. In these procedures, the physician uses an endoscope to maneuver a catheter down the esophagus, through the stomach, and into position within either the bile duct or pancreatic duct. The endoscopic view is projected on a video endoscopy monitor. A quantity of radiographically opaque dye is then injected through the catheter retrograde into the selected duct. Subsequently, the duct is viewed fluoroscopically on a video fluoroscopy monitor, and the X-rays illuminate the dye to reveal the anatomy and possible abnormalities in the biliary system. If the dye does not properly fill the duct, the catheter may have to be repositioned under endoscopic supervision to permit further infusion of dye. When further dye has been infused, the physician again views the duct fluoroscopically on the video fluoroscopy monitor. After the procedure has been completed within the first duct, the physician uses the endoscope to reposition the catheter within the other of the bile or pancreatic duct, and the dye injection procedure is repeated. The physician then switches back to the, fluoroscopic view to visualize the second duct. Depending upon the success of the initial dye injection into the second duct, the physician may again have to switch to the endoscope to reposition the catheter within the second duct, and then switch back to the fluoroscope to view the duct.

During steps when the physician is using the endoscope rather than the fluoroscope, fluoroscopy may inadvertently continue while the physician'attention is occupied with the endoscopic procedure. The patient and attending medical personnel are thus exposed unnecessarily to excessive dosages of X-rays during those periods when the physician is not actually viewing the fluoroscope. Thus, there is a need to provide a means for avoiding this accidental overexposure of the patient and attending medical personnel to X-rays during periods when the fluoroscope is not actually being used by the physician.

Apparatus has been developed to address the problem of accidental over-radiation of a patient and attending medical personnel during surgical procedures involving fluoroscopy and endoscopy. In my U.S. Pat. Nos. 4,993,464 and 5,127,444, which patents are incorporated herein by reference, apparatus is described in which video outputs from a fluoroscope and an endoscope are connected to a switching device. The physician uses the switching device to select from between the endoscope video output and the fluoroscope video output for viewing on a single video monitor. When the endoscope video output is selected for viewing, the switching device automatically deactivates the X-ray generator of the fluoroscope. When the switching device is actuated to select the fluoroscope video signal for viewing on the monitor, the switching device automatically reactivates the X-ray generator. In this manner, over-radiation of the patient during periods when the fluoroscope is not being used is avoided.

While the device disclosed in my aforesaid U.S. Pat. Nos. 4,993,464 and 5,127,444 represents a significant solution to the problem of accidental over-radiation, it suffers certain drawbacks, foremost among these being that the device requires that the standard fluoroscope foot pedal for activating the fluoroscope must be replaced in favor of a special foot pedal which allows integration of the switching device during the combined endoscopic/fluoroscopic procedure. At the termination of its use, the switching device must be removed and the special foot pedal reestablished in an uninterrupted fashion for resumption of normal foot pedal control of the fluoroscope. It would therefore be desirable if there were an apparatus which would utilize the existing standard fluoroscope pedal.

In addition, on occasion the physician may need to view the fluoroscope image while an assistant maintains observation of the endoscope view, or vice versa. However, the arrangement disclosed in my aforementioned U.S. Pat. Nos. 4,993,464 and 5,127,444 always disables the endoscope view when the fluoroscope X-ray generator is enabled. On those occasions when simultaneous observation of the endoscope and fluoroscope views is needed, it would be desirable to permit the fluoroscope view to be observed without discontinuing the display of the endoscope view, while maintaining the advantages provided by the arrangement disclosed in my aforementioned U.S. Pat. Nos. 4,993,464 and 5,127,444.

SUMMARY OF THE INVENTION

As will be seen, the present invention overcomes these and other drawbacks associated with prior art devices for preventing accidental over-radiation of a patient and attending medical personnel during surgical procedures involving fluoroscopy and endoscopy. Stated generally, the present invention comprises an apparatus for simultaneous actuation of multiple foot pedal operated switches to control endoscopy and fluoroscopy equipment. The apparatus automatically disables the X-ray generator of the fluoroscope whenever the fluoroscope video signal is not being displayed on the operating room monitor. The apparatus employs the existing standard fluoroscope foot pedal for switching the X-ray generator of the fluoroscope. Hence problems associated with disconnecting the original pedal and replacing it with a special pedal to allow interposition of the switching device, and then removing the special switching device upon completion of the procedure to reestablish normal fluoroscope operation, are avoided.

Stated somewhat more specifically, the disclosed embodiments of the present invention comprises an apparatus for performing a surgical procedure involving endoscopy and fluoroscopy. According to one embodiment, a video switching device has a foot pedal associated therewith for operating a switch to actuate the video switching device to select from between multiple video inputs for output to a single video monitor. A fluoroscope has an X-ray generator, a foot pedal associated therewith for operating a switch to enable the X-ray generator, and a video output connected to the video switching device. An endoscope has a video output connected to the video switching device. The fluoroscope foot pedal and the video switching device foot pedal are received within a housing, the housing having a lid movably mounted thereto and configured such that downward movement of the lid depresses both the fluoroscope foot pedal and the video switching device foot pedal. Thus a downward movement of the lid of the housing will actuate the fluoroscope foot pedal to enable the X-ray generator and will also operate the video switching device foot pedal to actuate the video switching device to select the fluoroscope video output for output to the monitor. Releasing the lid will permit the fluoroscope foot pedal to return to its normal state, disabling the X-ray generator, and will also permit the video switching device foot pedal to return to its normal state, actuating the video switching device to select the endoscope video output for output to the monitor. In this manner, the X-ray generator is enabled only when the fluoroscope video signal is being displayed on the monitor, thereby avoiding accidental over-radiation of the patient and attending medical personnel.

In a second embodiment the lid of the housing is divided into two sections, one of which is independently movable with respect to the other. Depressing one section of the lid actuates the fluoroscope foot pedal to enable the fluoroscope X-ray generator, and depressing the second section of the lid depresses the video switching device foot pedal and actuates the video switching device to select the fluoroscope view for display on the main monitor. A coupling mechanism is provided such that stepping on the second section of the lid also causes the first section of the lid to be depressed, thereby simultaneously depressing both foot pedals. In this manner the fluoroscope X-ray generator is enabled, and the video switching device is actuated to display the fluoroscope view on the main monitor. However, the coupling arrangement is such that the first section of the lid can be depressed independently of the second section. Thus if the physician wishes to enable the fluoroscope without discontinuing display of the endoscope image on the main monitor, he can depress the first section of the lid. The fluoroscope X-ray generator is thus enabled without actuating the video switching device to display the fluoroscope view on the main monitor. In this manner the endoscope view continues to be displayed on the main monitor, and the physician can observe the fluoroscope view on a second video monitor dedicated to the fluoroscope view.

In a third embodiment, the foot pedal for actuating the switch which controls the video switching device is eliminated, and the switch is built into the housing. The foot pedal which enables the fluoroscope generator continues to be received within the housing. Depressing the hinged lid of the housing actuates the built-in switch for controlling the video switching device and simultaneously depresses the endoscope foot pedal to enable the X-ray generator. The built-in switch may be used either with a housing having a single hinged lid or in a housing with the dual hinged lids. In the latter instance the built-in switch is actuated by stepping on the second section of the lid, which also actuates the first section of the lid to depress the fluoroscope foot pedal and actuate the X-ray generator. Optionally the physician may step on the first section of the lid to depress the fluoroscope foot pedal and actuate the X-ray generator without actuating the built-in switch for controlling is the video switching device.

Thus, it is an object of the present invention to provide an apparatus for minimizing exposure of a patient and attending medical personnel to X-rays during procedures involving fluoroscopy and another video-assisted visualization technique.

It is another object of the present invention to provide a fluoroscopy apparatus wherein the X-ray generator is enabled only when the physician performing the procedure is actually viewing the fluoroscope.

It is still another object of the present invention to provide an apparatus for minimizing exposure of a patient and attending medical personnel to X-rays during procedures involving fluoroscopy and another video-assisted visualization technique which does not require removal of the standard fluoroscope foot pedal.

Another object of the present invention is to provide an apparatus for minimizing exposure of a patient and attending medical personnel to X-rays during procedures involving fluoroscopy and another video-assisted visualization technique wherein a single action of the physician'foot is normally operative to enable the fluoroscope X-ray generator and simultaneously select the fluoroscope view for display on the main monitor, but wherein the physician can selectively enable the fluoroscope X-ray generator without simultaneously selecting the fluoroscope view for display on the main monitor.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
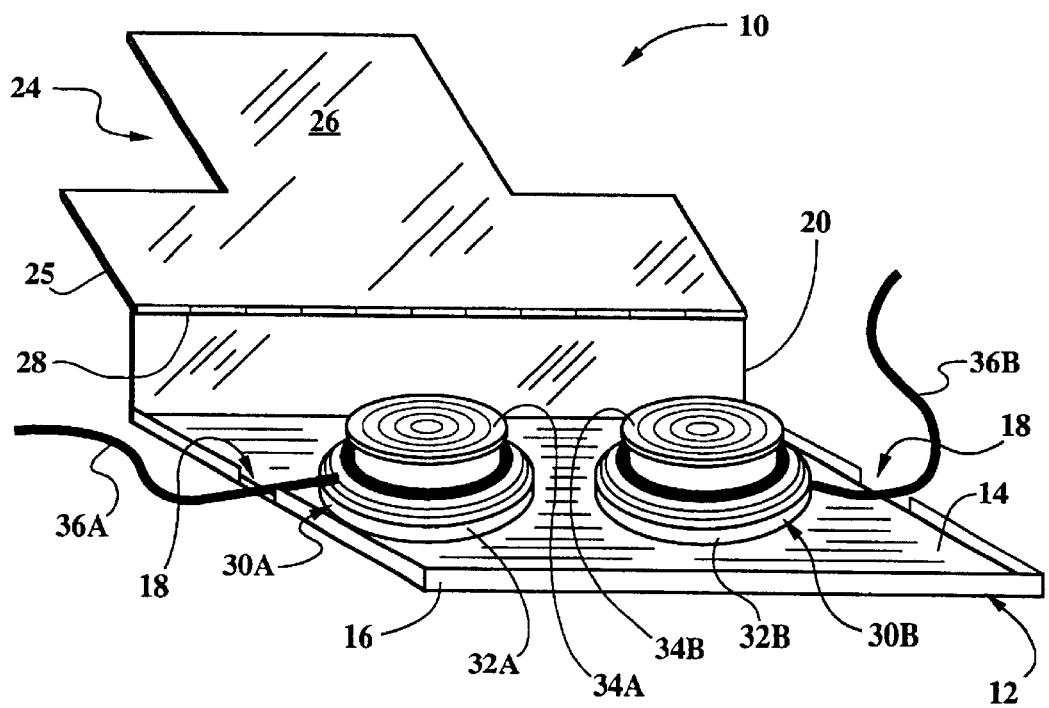
FIG. 1 is an isometric view of an apparatus according to the present invention for simultaneous actuation of multiple foot pedal operated switches, showing the lid of tie apparatus open to reveal interior detail.
Figure 3:
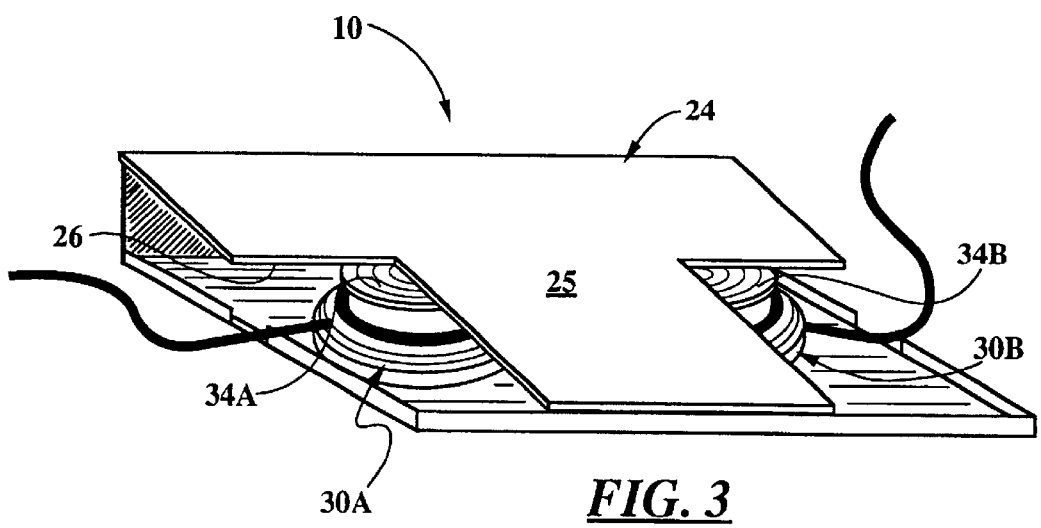
FIG. 3 is an isometric view of the apparatus of FIG. 1 showing the lid closed in its operating configuration.

Referring now in more detail to the drawings, in which like numerals indicate like elements throughout the several views, FIG. 1 shows a multi-pedal housing 10 for simultaneous switching of multiple foot pedals. The housing 10 includes a base 12 having a slip-resistant mat 14 located on its upper surface. A slip-resistant mat may also be provided on the lower surface of the base if desired. An upstanding lip 16 extends around the periphery of the base 12 and has notches 18 formed therein on opposing lateral sides. An upstanding wall projects upward along the rear edge of the base 12. A lid 24 is pivotably mounted to the upper edge of the upstanding wall by means of a hinge 28. A recess is thus defined within the housing 10 beneath the lid 24. The lid includes an upper surface 25 and a lower surface 26 (the terms "upper" and "lower" referring to the lid in its normal operating orientation, as depicted in FIG. 3). The upper surface 25 of the hinged lid 24 comprises a pedal surface and, accordingly, may be provided with a non-skid finish if desired. The hinge 28 may be spring loaded to bias the lid 24 to a normal position, as will be hereinbelow described.

In the disclosed embodiment the lid 24 has cutouts formed along its lateral edges such that the lid assumes the shape of a "T." The purpose of the cutouts is to ensure that the user presses his foot on the central portion of the lid 24 to prevent bending or torquing of the lid. However it will be appreciated that the cutouts are not essential to the operation of the housing 10 and that other arrangements for encouraging the user to exert the force on the central portion of the lid may be used. Such alternate arrangements might include providing a textured surface on the central portion of the lid 24 which is different from the surface of the marginal portions of the lid, whereby the user can tell tactilely whether his foot is on the intended portion. Even further, a full-width lid may be used without any means for ensuring that the user presses down on a predefined portion of the lid.

As further shown in FIG. 1, two foot pedals 30A, 30B are positioned on the base 12 within the recess of the housing 10. The foot pedal 30A comprises a base 32A with a pedal member 34A movably mounted to the base 32A and projecting upward therefrom. Similarly the foot pedal 30B comprises a base 32B with a pedal member 34B movably mounted to the base 32B and projecting upward therefrom. Each of the pedal members 34A, 34B is adapted to be depressed by downward pressure of a foot on the upper surface of the pedal member. Each of the foot pedals 30A, 30B has an electrical switch associated therewith, as will be explained below, such that depressing the pedal members 34A, 34B actuates the switches.

The bases 32A, 32B of the foot pedals 30A, 30B rest on the slip-proof mat 14 within the housing 10, and the upstanding lip 16 and upstanding wall 20 prevent the pedals from moving. Cables 36A, 36B connected to the respective foot pedals 30A, 30B exit the housing at their respective sides. If the foot pedals 30A, 30B are of different heights, the lower of the two foot pedals may be shimmed, such as by further thicknesses of the non-skid mat material, to bring the upper surface of the pedal members 34A, 34B of the two foot pedals 30A, 30B to the same height.

If desired, fasteners, such as fabric fasteners of the cooperating hook-and-loop type (e.g. Velcro® fasteners), can be provided to further secure the foot pedals 30A, 30B to the base, or can be employed to retain the cables 36A, 36B to prevent the cables from interfering with normal operation of the pedal members 34A, 34B.

Figure 2:
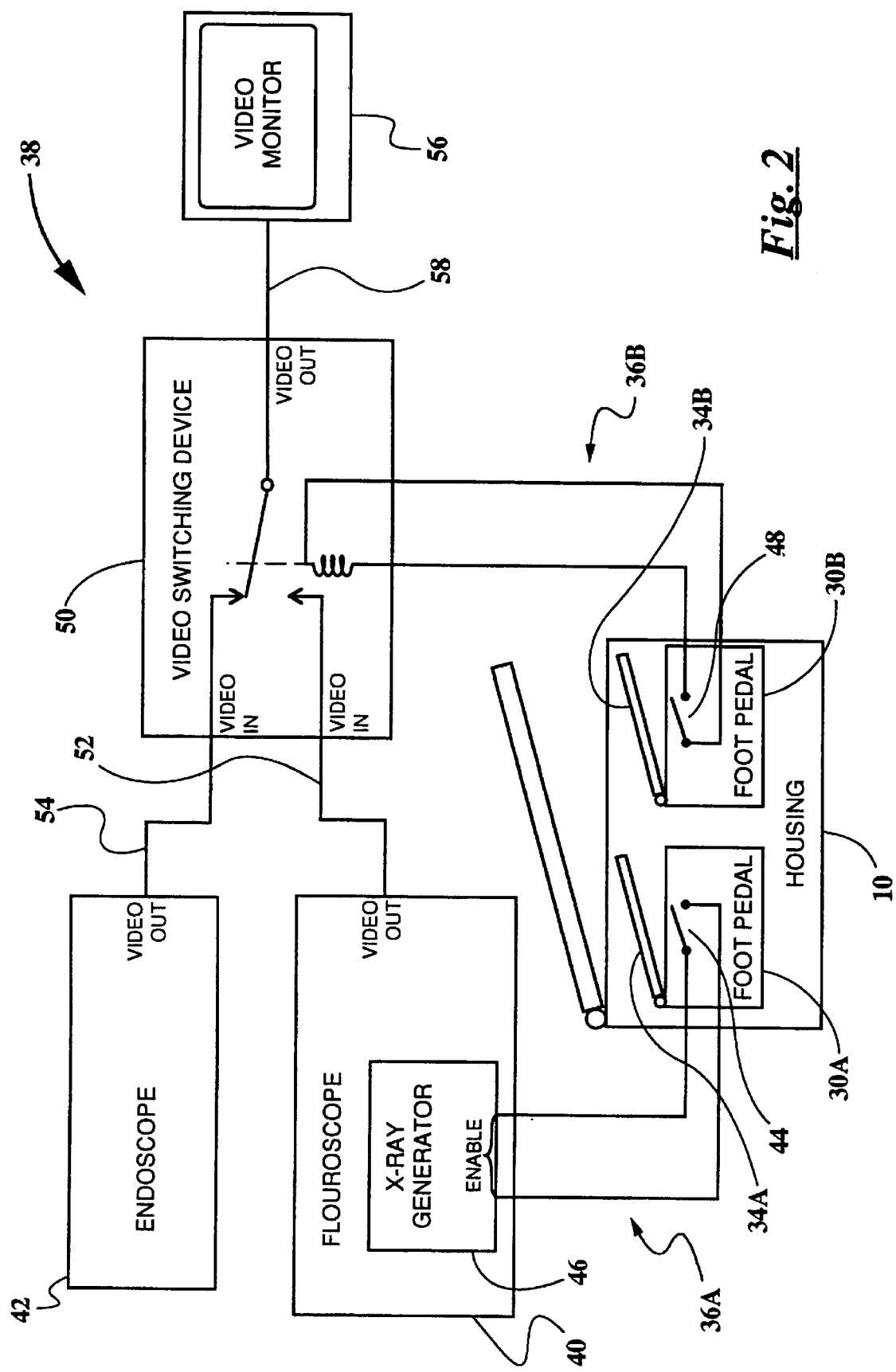
FIG. 2 is a schematic diagram showing the apparatus of FIG. 1 with the multiple foot pedal operated switches configured to operate fluoroscopic and endoscopic medical apparatus.

An apparatus 38 which employs the multi-pedal housing 10 in conjunction with a video fluoroscope 40 and a video endoscope 42 is illustrated schematically in FIG. 2. The foot pedal 30A has associated therewith a switch 44 of conventional design which is connected by means of the cable 36A to the fluoroscope 40. The fluoroscope 40 comprises an X-ray generator 46. The fluoroscope 40 of the disclosed embodiment is the Philips Diagnost 92, though it will be appreciated that other fluoroscopes are easily adapted to the present invention. The fluoroscope foot pedal 30A operates in a conventional manner to close the switch 44 when its pedal member 34A is depressed to enable the X-ray generator 46 of the fluoroscope 40. When downward pressure on the pedal member 34A is released, the foot pedal 30A returns to its normal state in which the switch 44 is open, and the X-ray generator 46 is disabled.

The second foot pedal 30B has associated therewith a switch 48 of conventional design which is connected by means of the cable 36B to a video switching device 50. The video output from the fluoroscope 40 is connected to the video switching device 50 by means of a signal path 52, and the video output from the video endoscope 42 is connected to the video switching device 50 by means of a signal path 54. The video endoscope 42 of the disclosed embodiment is the Olympus CV-100, though it will again be appreciated that other brands and models of video endoscope systems will be easily adapted to the present invention. In its normal state the video switching device 50 selects the video signal from the endoscope for output to a video monitor 56 by means of a signal path 58. When the pedal member 34B of the foot pedal 30B is depressed, the switch 48 closes, actuating the video switching device 50 to select the video signal of the fluoroscope 40 for output to the video monitor 56. When the pedal member 34B of the foot pedal 30B is released, the foot pedal 30B returns to its normal state wherein the switch 48 is open, and the video switching device 50 selects the video signal of the endoscope 42 for output to the video monitor 56

FIG. 3 shows the multi-pedal housing 10 with the hinged lid 24 closed. In this position, the lower surface 26 of the lid 24 bears against the pedal members 34A, 34B of each of the foot pedals 30A, 30B. When a downward force is exerted against the upper surface 25 of the lid 24, the lid 24 pivots about its hinge 28 and depresses the pedal members 34A, 34B of the foot pedals 30A, 30B. In this manner, a single downward movement of the hinged lid 24 of the housing 10 will simultaneously actuate both of the switches 44, 48 associated with the respective foot pedals 30A, 30B.

The foot pedals 30A, 30B include springs (not shown) which return the pedal members 34A, 34B to their raised position after an applied force has been released. Under normal operating circumstances, the force of these springs should be more than sufficient to overcome the weight of the lid 24 and any friction of the hinge 28 and return the pedal members 34A, 34B to their raised position. However, to prevent the weight of the lid 24 or a moderately binding hinge 28 from continuing to depress the foot pedals 30A, 30B after the downward force on the lid has been released, the lid 24 is spring biased to a normal position in which the lid rests lightly on the undepressed pedal members 34A, 34B.

Use of the apparatus 38 will now be described. The multi-pedal housing 10 can be used to operate the video fluoroscope 40 and the video endoscope 42, for example during surgical modalities involving video endoscopy used in conjunction with dye-injection studies under fluoroscopy at various times during the procedure. The hinged lid 24 of the housing 10 is opened, and the foot pedals 30A, 30B are positioned within the housing on the slip-proof mat 14 of the base 12. The cables 36A, 36B are extended out the sides of the housing 10 and connected to the X-ray generator 46 of the fluoroscope 40 and to the video switching device 50, respectively. The lid 24 is then closed until the lower surface 26 of the lid 24 rests against the respective pedal members 34A, 34B of each of the foot pedals 30A, 30B.

During a procedure, when the physician wishes to select the fluoroscope view for display on the monitor 56, the physician places his foot on the upper surface 25 of the hinged lid 24 and exerts a downward force. The downward pressure of the lid 24 against the pedal members 34A, 34B of the foot pedals 30A, 30B actuates both switches 44, 48 simultaneously. Thus the X-ray generator 46 of the fluoroscope 40 is enabled, and simultaneously the video switching device 50 selects the fluoroscope video signal for display on the monitor 56. When the physician wishes to redisplay the endoscope view on the monitor 56, the physician simply releases the lid 24 of the housing 10 with his foot, thereby releasing both foot pedals 30A, 30B and permitting them to return to their normal states. The switch 48 thus opens and actuates the video switching device 50 to select the video signal of the endoscope 42 for display on the monitor 56. Simultaneously, the switch 44 opens and disables the X-ray generator 46 of the fluoroscope 40.

As will be appreciated, when the foot pedal housing 10 of the present invention is used in the manner described above to control the fluoroscope 40 and the video switching device 50, the X-ray generator 46 of the fluoroscope 40 is enabled only when the fluoroscope video signal is being displayed on the video monitor 56. When the fluoroscope video signal is not being displayed on the monitor 56, the X-ray generator 46 is automatically disabled. In this manner accidental over-radiation of the patient and attending medical personnel is avoided.

Figure 4:
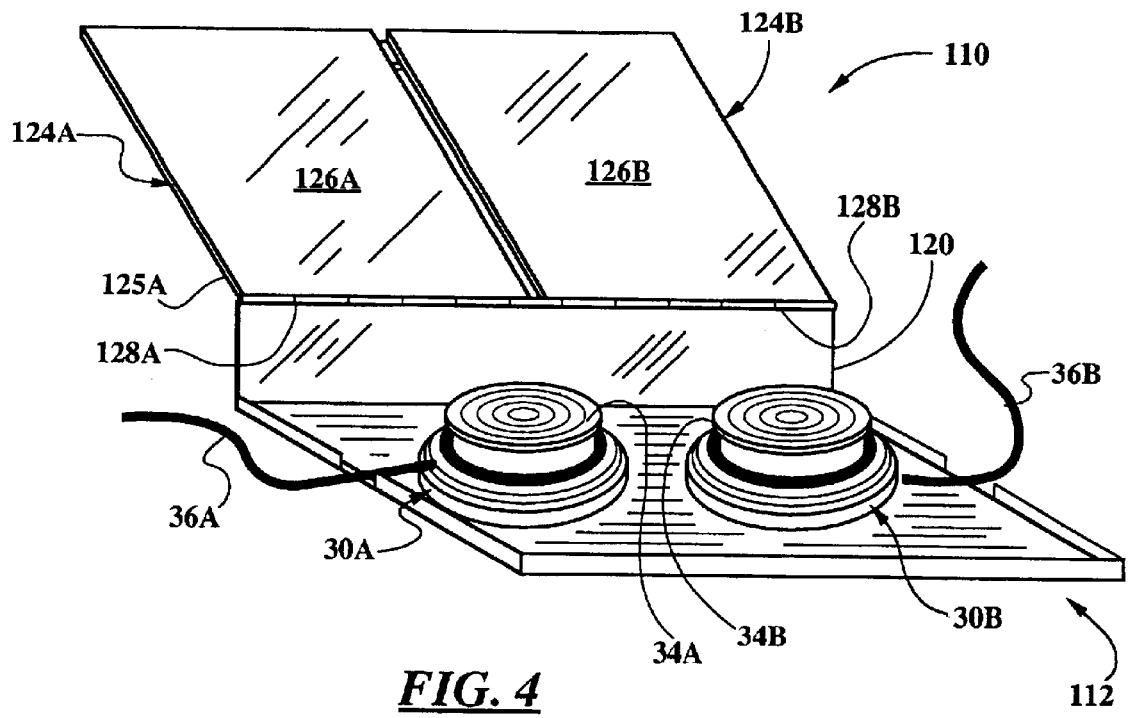
FIG. 4 is an isometric view of a second embodiment of an apparatus according to the present invention for simultaneous actuation of multiple foot pedal operated switches, showing the lids of the apparatus open to reveal interior detail.
Figure 6:
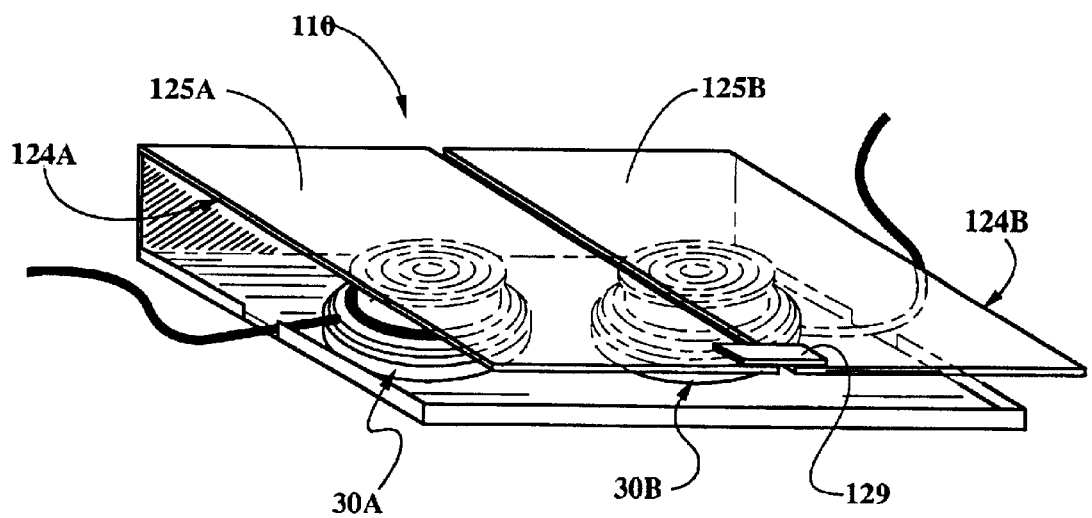
FIG. 6 is an isometric view of the apparatus of FIG. 4 showing the lids closed in their operating configuration.

FIG. 4 illustrates a second embodiment of a housing 110 for simultaneous switching of multiple foot pedals. Like the, housing 10 of the previous embodiment, the housing 110 includes a base 112 and an upstanding wall 120 projecting upward along the rear edge of the base 112. A first lid 124A is pivotably mounted to the upper edge of the upstanding wall 120 at the left side of the housing 110 by means of a first hinge 128A. The first lid 124A includes an upper surface 125A and a lower surface 126A (the terms "upper" and "lower" referring to the first lid 124A in its normal operating orientation, as depicted in FIG. 4). A second lid 124B is pivotably mounted to the upper edge of the upstanding wall 120 on the right side of the housing 110 by means of a second hinge 128B. The second lid 124B includes an upper surface 129B and a lower surface 126B. The hinges 128A, 128B are spring loaded to bias the lids 124A, 124B to a normal position in the same manner as the lid 24 of the previously described embodiment.

A tab 129 is attached to the second lid 124B and projects across at least a portion of the upper surface 125A of the first lid 124A. When the second lid 124B is depressed, the tab 129 bearing against the upper surface 125A of the first lid 124A causes the first lid to be depressed. However, it will be appreciated that when the first lid 124A is depressed, it does not confront the tab 129 such that the first lid 124A can be depressed independently of the second lid 124B.

It will be appreciated that similar results could be obtained by forming a tab on the first lid 124A which would extend below the lower surface 126B of the second lid 124B. When the second lid 124B is depressed, its lower surface 126B would confront the tab and cause the first lid 124A to be displaced downward. However when the first lid 124A is depressed, the tab would not engage the second lid 124B such that the first lid 124A would be movable independently of the second lid 124B. Other modifications, such as a pin selectively insertable through both of the lids 124A, 124B to couple the lids to cause both lids to be depressed and actuate both devices simultaneously, and selectively removable to permit independent movement of the lids, will occur to those skilled in the art.

Figure 5:
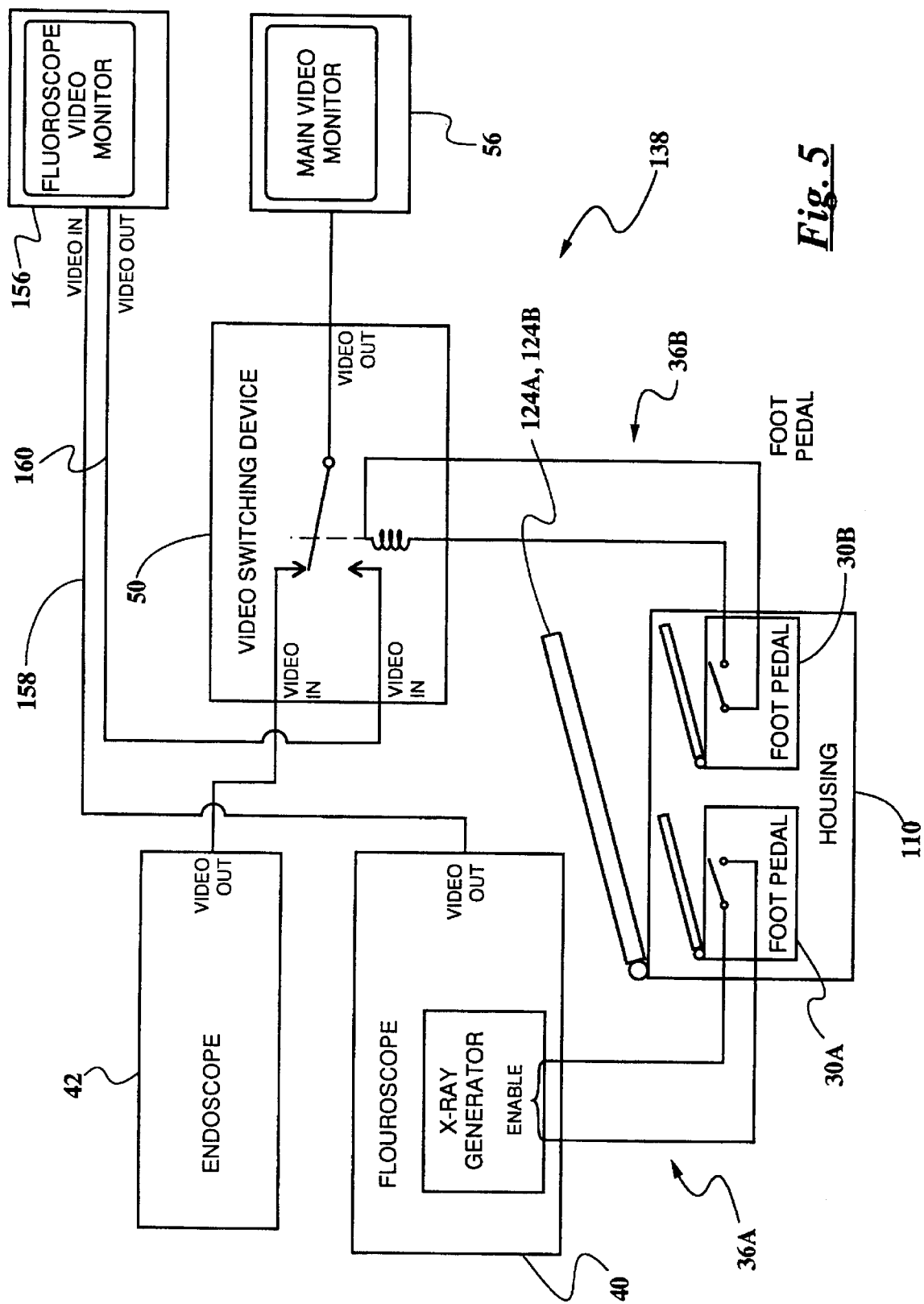
FIG. 5 is a schematic diagram showing the apparatus of FIG. 4 with the multiple foot pedal operated switches configured to operate fluoroscopic and endoscopic medical apparatus.

FIG. 5 is a schematic illustration of an apparatus 138 which employs the foot pedal housing 110 in conjunction with the video fluoroscope 40 and video endoscope 42. Video connections between the video endoscope 42 and the video switching device 50 are the same as for the previously described embodiment 38. However, unlike the previous embodiment 38, the video output from the fluoroscope 40 is sent to a dedicated fluoroscope video monitor 156 via a signal path 158. The fluoroscope video signal is then passed through the fluoroscope video monitor 156 to the video switching device 50 via a signal path 160. If a fluoroscope video monitor is used which lacks an output terminal, a "T" connector can be connected along the signal path 159 to split the signal to the signal path 160.

Operation of the apparatus 138 will now be explained. The two foot pedals 30A, 30B are positioned within the housing 110, the fluoroscope foot pedal 30A being disposed beneath the first lid 124A, and the video switching device foot pedal 30B being disposed beneath the second lid 124B.

Figure 7:
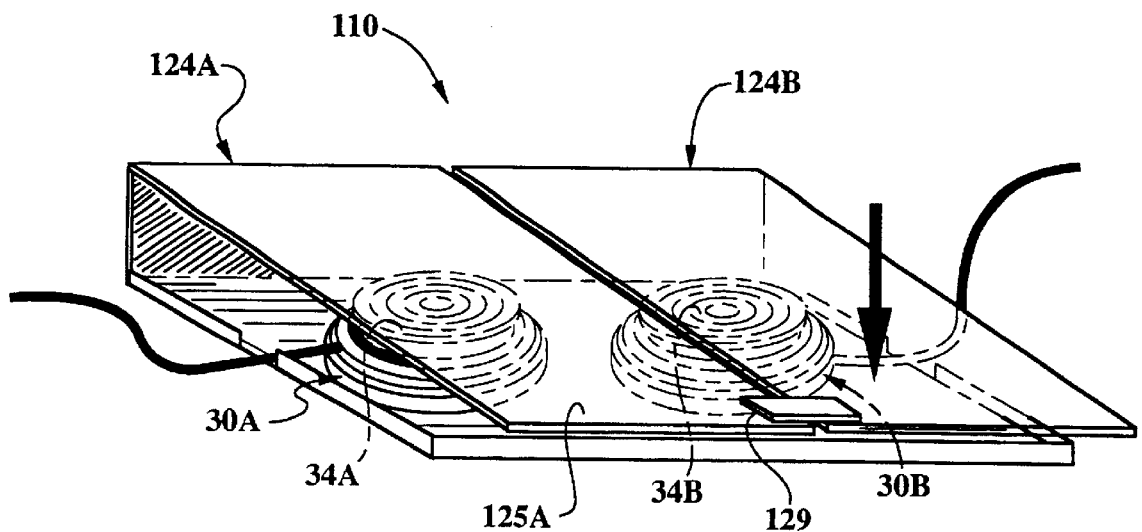
FIG. 7 is an isometric view of the apparatus of FIG. 4 showing both lids depressed to actuate both foot pedals housed therewithin.

In normal operation as illustrated in FIG. 7, the second lid 124B is conveniently located on the right side of the housing 110 adjacent the physician's right foot when the housing is in the position customarily occupied by a foot pedal, that is, between the physician's legs. The physician depresses the second lid 124B, and this downward movement of the second lid 124B causes the pedal member 34B of the video switching device foot pedal 30B to be depressed, closing the switch 48 and actuating the video switching device 50 to select the fluoroscope view for display on the main video monitor 56. As the second lid 124B is depressed, the tab 129 confronts the upper surface 125A of the first lid 124A, causing the first lid to be displaced downward. This downward movement of the first lid 124A causes the pedal member 34A of the fluoroscope foot pedal 30A to be depressed, thereby closing the switch 44 and enabling the X-ray generator 46. Thus the X-ray generator 46 of the fluoroscope 40 is enabled concurrently with selection of the fluoroscope view for display on the video monitor 56. When the physician releases downward pressure from the second lid 124B, both foot pedals 30A, 30B are permitted to return to their normal state. Consequently both switches 44, 48 open, disabling the X-ray generator 46 of the fluoroscope 40 is concurrently with selection of the endoscope view for display on tie video monitor 56.

Figure 8:
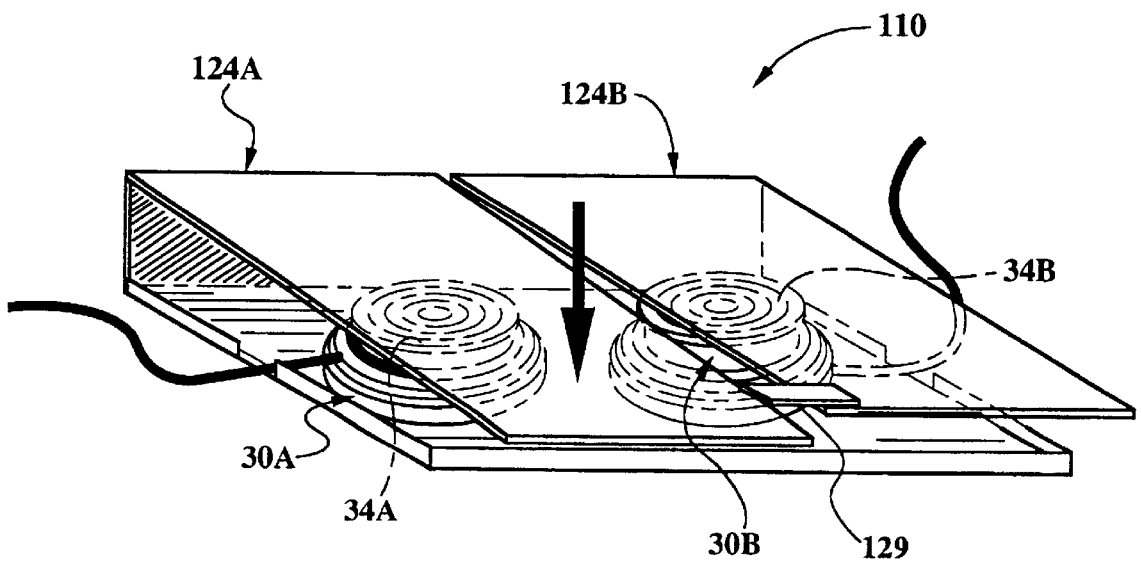
FIG. 8 is an isometric view of the apparatus of FIG. 4 showing one lid selectively depressed independently of the second to actuate only the fluoroscope X-ray generator foot pedal housed therewithin.

Should the physician ever want to enable the fluoroscope 40 without removing the endoscope view from the main video monitor 56, he can simply depress the first lid 124A as shown in FIG. 8. As previously explained, the first lid 124A can be displaced downward independently of the second lid 124B. Depressing the first lid 124A thus depresses the pedal member 34A of the fluoroscope foot pedal 30A, closing the switch 44 and causing the X-ray generator 46 of the fluoroscope 40 to be enabled. However, since the second lid 124B is not depressed, the video switching device foot pedal 30B is not actuated to deselect the endoscope view for display on the main video monitor 56. The physician can thus view the fluoroscope view on the separate fluoroscope monitor 156 while an assistant continues to watch the endoscope view on the main video monitor 56.

Figure 9:
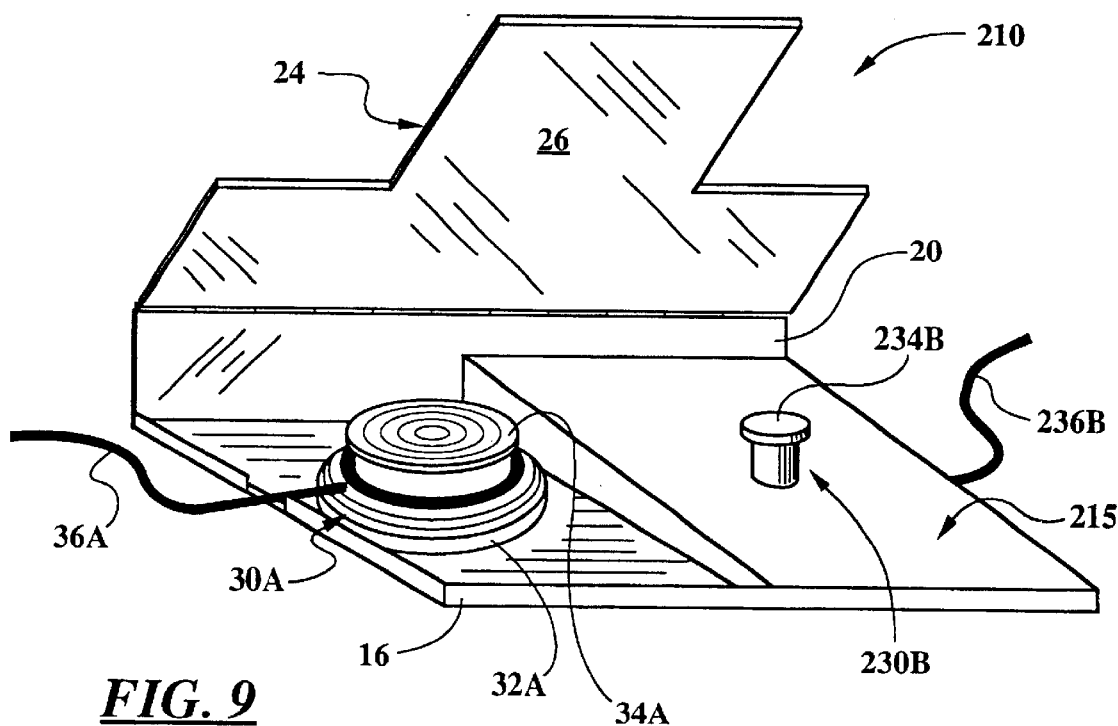
FIG. 9 is an isometric view of a third embodiment of an apparatus for simultaneous actuation of multiple foot pedal operated switches, showing the lid of the apparatus open to reveal interior detail.

A third embodiment of a foot pedal housing 210 is illustrated in FIG. 9. A casing 215 is mounted within the housing 210 on the right side of the base 12. The fluoroscope foot pedal 34A is positioned within a recess defined within the housing 210 on the left side of the base 12. A contact switch 234B of the "plunger" or "button" variety is mounted to the casing 215 such that the switch 234B is for all intents and purposes permanently mounted to the housing 210. The switch 234B is arranged such that the upper surface of a plunger member 234B is at approximately the same height above the base 12 as the pedal member 34A of the fluoroscope foot pedal assembly 30A. A cable 236B connects the switch 234B with the video switching device 50. Thus a downward movement of the lid 24 of the housing 210 depresses the pedal member 34A of the fluoroscope foot pedal assembly 30A and simultaneously depresses the plunger member 234B of the switch 234B, thereby enabling the X-ray generator of the fluoroscope concurrently with the video switching device selecting the fluoroscope view for display on the video monitor.

Figure 10:
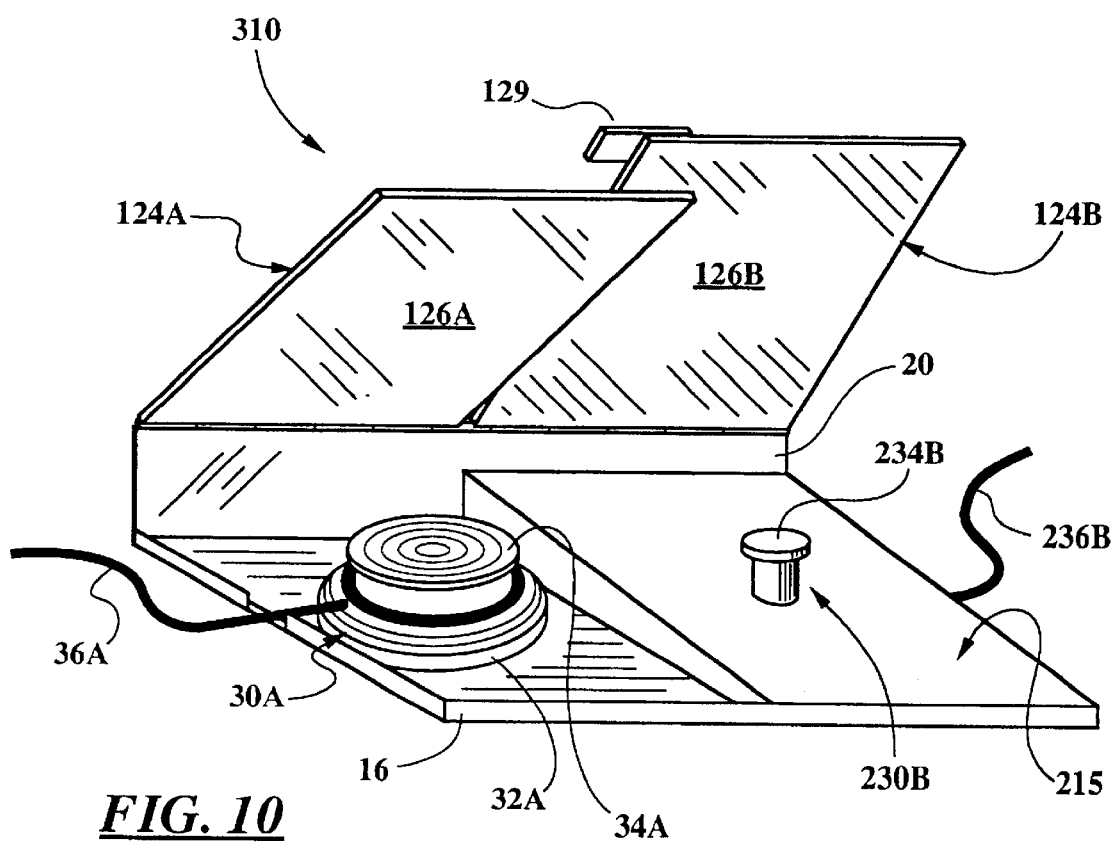
FIG. 10 is an isometric view of a fourth embodiment of an apparatus for simultaneous actuation of multiple foot pedal operated switches, showing the lids of the apparatus open to reveal interior detail.

A fourth embodiment of a foot pedal housing 310 is depicted in FIG. 10. The housing 310 is identical to the housing 210 of the previously described embodiment with the exception that the lid is divided into two parts 124A, 124B, as in the housing 110 previously described. As in the housing 110, a tab 129 selectively couples the two lids 124A, 124B such that depressing the second lid 124B causes the first lid 124A to be depressed. However, tab 129 is arranged such that the first lid 124A is movable independently of the second lid 124B. When the physician desires to enable the X-ray generator and display the fluoroscope view on the main video monitor, he depresses the second lid 124B. The downward movement of the second lid 124B depresses the plunger 234B of the integrally mounted switch 230B, causing the video switching device to select the fluoroscope view for display on the main video monitor. Simultaneously the tab 129 causes the first lid 124A to be depressed, thereby depressing the pedal member 34A of the fluoroscope foot pedal assembly 30A and thereby enabling the X-ray generator. Should the physician desire to enable the X-ray generator without deselecting the endoscope view on the main video monitor, he depresses the first lid 124A. The downward movement of the first lid 124A depresses tile pedal member 34A of the fluoroscope foot pedal assembly 30A and enables the X-ray generator. However, since the second lid 124B is not depressed, the integral switch 230B is not actuated, and the video switching device does not deselect the endoscope view.

While the foregoing embodiments have all been disclosed with respect to foot pedal housings for use with a video endoscope and a video fluoroscope, it will be understood that the present invention is not so limited, and that the foot pedal housing of the present invention can be easily adapted to other types of equipment which are actuated by foot pedals and for which coordination of the equipment is desirable. Further, while the foot pedal operated switches of the foregoing embodiments are operative only to turn a device on or off or to cause a device to select from between two video signals for output to a video monitor, it will be understood that the present invention can be adapted to any device wherein actuation of a foot pedal changes a state of the device.

Further, while the foregoing embodiments have all been disclosed with respect to a foot pedal housing for use with only one or two foot pedals, it will be appreciated that, if desired, the foot pedal housing may be configured to receive a greater number of foot pedals therewithin. Such configurations of multiple foot pedals might entail actuating all of the pedals simultaneously, one or more of the pedals independently of the others, or any other combination as may occur to one of ordinary skill in the art.

Finally, it will be understood that the foregoing embodiments have been disclosed by way of example, and that other modifications may occur to those skilled in the art without departing from the scope and spirit of the appended claims.

What is claimed is:

1. An apparatus for coordinating the operation of multiple devices actuated by switches, comprising:

a housing having a base and having a lid movably mounted thereto, said housing defining a recess therewithin;

a freestanding foot pedal assembly having a base and a pedal member which is downwardly movable with respect to said base, said pedal member being adapted to be depressed by downward pressure exerted by the foot of a user, and said freestanding foot pedal assembly having a first switch operatively associated therewith which is actuated by a downward movement of said pedal member;

said freestanding foot pedal assembly being disposed within said recess defined within said housing such that a downward movement of said lid displaces said pedal member of said freestanding foot pedal assembly to actuate said first switch;

a second switch disposed such that said downward movement of said lid of said housing actuates said second switch;

a first device operatively associated with said first switch and responsive to actuation thereof for changing a state of said first device; and a second device operatively associated with said second switch and responsive to actuation thereof for changing a state of said second device;

whereby said downward movement of said lid actuates said first and second switches together to change said states of said first and second devices concurrently.

2. The apparatus of claim 1, wherein said freestanding foot pedal assembly comprises a first freestanding foot pedal assembly, and said apparatus further comprising:

a second freestanding foot pedal assembly having a base and a pedal member which is downwardly movable with respect to said base, said pedal member of said second foot pedal assembly being adapted to be depressed by downward pressure exerted by the foot of a user, and said second switch being operatively associated with said second freestanding foot pedal assembly such that a downward movement of said pedal member actuates said second switch;

said second freestanding foot pedal assembly being disposed within said recess defined within said housing such that a downward movement of said lid displaces said pedal member of said second freestanding foot pedal assembly to actuate said second switch.

3. The apparatus of claim 1, wherein said lid of said housing comprises first and second lid sections which are independently movable with respect to one another.

4. The apparatus of claim 3, further comprising a coupling member operatively associated with said first and second lid sections and being configured such that a downward movement of said second lid section causes a downward movement of said first lid section, said coupling member further being configured such that said first lid section is downwardly movable independently of said second lid section.

5. The apparatus of claim 4, wherein said coupling member comprises a tab attached to said second lid section and extending over a portion of said first lid section, whereby when said second lid section is displaced downward, said tab confronts said first lid section and displaces said first lid section downward.

6. The apparatus of claim 4, wherein said coupling member comprises a tab attached to said first lid section and extending beneath a portion of said first lid section, whereby when said second lid section is displaced downward, said second lid section confronts said tab and displaces said first lid section downward.

7. An apparatus for performing a surgical procedure involving endoscopy and fluoroscopy, comprising:

a housing having a base and having a lid movably mounted thereto, said housing defining a recess therewithin;

a freestanding fluoroscope foot pedal assembly having a base and a pedal member which is downwardly movable with respect to said base, said pedal member being adapted to be depressed by downward pressure exerted by the foot of a user, and said fluoroscope foot pedal assembly having a first switch operatively associated therewith which is actuated by a downward movement of said pedal member;

said freestanding fluoroscope foot pedal assembly being disposed within said recess defined within said housing such that a downward movement of said lid of said housing displaces said pedal member of said freestanding fluoroscope foot pedal assembly to actuate said first switch;

a second switch disposed such that said downward movement of said lid of said housing actuates said second switch;

a video switching device having first and second video inputs, said video switching device normally being operative to select said second video input for display on a video monitor, said video switching device being operatively associated with said second switch and responsive to actuation thereof for selecting said first video input for display on said video monitor;

a fluoroscope having a video output connected to said first video input of said video switching device, said fluoroscope further having an X-ray generator operatively associated with said first switch and responsive to actuation thereof for enabling said X-ray generator; and an endoscope having a video output connected to said second video input of video switching device;

whereby said video switching device normally selects said video output from said endoscope for display on said video monitor; and whereby a downward movement of said lid of said housing actuates said first switch to enable said X-ray generator of said fluoroscope and concurrently actuates said second switch to cause said video switching device to select said video output from said fluoroscope for display on said monitor.

8. The apparatus of claim 7, further comprising:

a freestanding video switching device foot pedal assembly having a base and a pedal member which is downwardly movable with respect to said base, said pedal member being adapted to be depressed by downward pressure exerted by the foot of a user, and said freestanding video switching device being operatively associated with said second switch so as to actuate said second switch upon a downward movement of said pedal member;

said freestanding video switching device foot pedal assembly being disposed within said recess defined within said housing such that a downward movement of said lid displaces said pedal member of said freestanding video switching device foot pedal assembly to actuate said second switch.

9. The apparatus of claim 8, wherein said pedal member of one of said freestanding fluoroscope foot pedal assembly and said freestanding video switching device foot pedal assembly is of a lower height than said pedal member of the other of said freestanding fluoroscope foot pedal assembly and said freestanding video switching device foot pedal assembly, said apparatus further comprising shim means for elevating said lower one of said freestanding fluoroscope foot pedal assembly and said freestanding video switching device foot pedal assembly such that said pedal members of said freestanding foot pedal assemblies are of equal height.

10. The apparatus of claim 8, wherein said housing comprises a base and an upstanding wall extending upward from said base, and wherein said lid movably mounted to said housing comprises said lid being pivotably mounted to said upstanding wall.

11. The apparatus of claim 10, wherein said lid is pivotably mounted to said upstanding wall by means of a spring-loaded hinge which normally biases said lid to a predetermined position.

12. The apparatus of claim 10, wherein said base further comprises a skid-resistant upper surface, and wherein said freestanding fluoroscope foot pedal and said freestanding video switching device foot pedal are disposed on said skid-resistant upper surface of said base.

13. The apparatus of claim 10, wherein said base comprises a plurality of peripheral edges, said apparatus further comprising a lip extending upward along at least one of said plurality of peripheral edges, whereby said freestanding fluoroscope foot pedal and said freestanding video switching device foot pedal are retained within said housing.

14. The apparatus of claim 7, wherein said lid of said housing comprises first and second lid sections which are independently movable with respect to one another.

15. The apparatus of claim 14, further comprising a coupling member operatively associated with said first and second lid sections and being configured such that a downward movement of said second lid section to actuate said video switching device causes a downward movement of said first lid section to actuate said fluoroscope X-ray generator, said coupling member further being configured such that said first lid section is downwardly movable independently of said second lid section to actuate said fluoroscope X-ray generator without actuating said video switching device.

16. The apparatus of claim 15, wherein said coupling member comprises a tab attached to said second lid section and extending over a portion of said first lid section, whereby when said second lid section is displaced downward, said tab confronts said first lid section and displaces said first lid section downward.

17. The apparatus of claim 15, wherein said coupling member comprises a tab attached to said first lid section and extending beneath a portion of said second lid section, whereby when said second lid section is displaced downward, said second lid section confronts said tab and displaces said first lid section downward.

* * * * *